United States Patent [19]

Stasz

[11] Patent Number: 4,674,498
[45] Date of Patent: Jun. 23, 1987

[54] ELECTRO CAUTERY SURGICAL BLADE

[75] Inventor: Peter Stasz, Minneapolis, Minn.

[73] Assignee: Everest Medical Corporation, Brooklyn Center, Minn.

[21] Appl. No.: 756,248

[22] Filed: Jul. 18, 1985

Related U.S. Application Data

[63] Continuation-in-part of Ser. No. 511,159, Jul. 6, 1983, abandoned.

[51] Int. Cl.$^4$ ............................................. A61B 17/39
[52] U.S. Cl. .................................. 128/303.14; 128/305; 604/22
[58] Field of Search ........... 128/303.1, 303.13–303.17, 128/303.19, 303 R, 305, 24 A; 604/22

[56] References Cited

U.S. PATENT DOCUMENTS

| | | | |
|---|---|---|---|
| 2,714,890 | 8/1955 | Vang | 128/24 A X |
| 3,815,604 | 6/1974 | O'Malley et al. | 604/22 |
| 3,862,630 | 1/1975 | Balamuth | 128/24 A |
| 4,091,813 | 5/1978 | Shaw et al. | 128/303.14 |
| 4,364,390 | 12/1982 | Shaw | 128/303.1 |

Primary Examiner—Lee S. Cohen
Attorney, Agent, or Firm—Orrin M. Haugen; Thomas J. Nikolai; Frederick W. Niebuhr

[57] ABSTRACT

An electro surgical instrument comprising a handle and a replaceable blade. The handle includes a blade receiving slot and means for clamping the proximal portion of the blade within the slot. Also formed internally of the handle and within the slot is a cavity for containing an electrical-to-mechanical transducer and a plurality of conductive terminal pad areas. The blade is provided with a pattern of conductors which are insulated from one another and which lead to contact pad areas on the distal portion of the blade. When the blade is appropriately inserted into the handle and clamped in place, the transducer abuts the blade and electrical contact is established to energize the conductors and the transducer whereby the blade may be vibrated at a frequency and amplitude to limit the build-up of tissue debris on the blade during an electro surgery procedure.

16 Claims, 19 Drawing Figures

ELECTRO CAUTERY SURGICAL BLADE

CROSS REFERENCE TO CO-PENDING APPLICATIONS

This application is a continuation-in-part of Ser. No. 511,159, filed July 6, 1983, now abandoned.

BACKGROUND OF THE INVENTION

I. Field of the Invention

The present invention relates to a surgical implement, and, more particularly, relates to an electro-cautery surgical tool which provides for different modes of operation including a standard surgical cutting blade or an electro-cautery blade and in which the blade is made to vibrate during use at a predetermined amplitude and frequency whereby cavitation results at the blade surface to free it of the build-up of organic debris.

II. Description of the Prior Art

Various prior art electro-cautery blades have been less than effective in that either a special material is required for the blades, or they comprise a combination of structures which are primarily ornamental and non-functional, and which require a considerable drive voltage which often cause undue tissue damage.

Some of the prior art devices do not allow for appropriate coupling of their blade member to their voltage sources and tend to be ineffectual.

Other types of prior art blades utilize extremely elaborate and complex electrical circuits with standard type of blade structures, which do not, in the end, accomplish a desirable result of an effective surgical blade capable of operation in more than one mode.

One of the most severe problems with the prior art is the adhesion of charred tissue and blood to the blade which shorts out the two conductors, and therefore, renders the blade useless as an electro-cautery device.

The present invention provides an electro-cautery surgical tool which, by utilizing state-of-the-art semiconductor masking technology, can be designed to function as a standard surgical blade, or as an electro-cautery blade. The present invention also provides an electro-cautery surgical tool which includes a capacitive blade. An important feature of the present invention is the provision of a piezo-ceramic, or other like element, coupled to a surgical blade for vibrating the blade so as to produce a cavitation effect which cleans the blade continuously during use.

SUMMARY OF THE INVENTION

The general purpose of the present invention is to provide an electro-cautery tool which can be utilized as a standard surgical cutting blade with a sharp edge when no electrical power is applied to it; as an electro-cautery blade when a high voltage is applied between conductive surfaces sufficient to create a discharge for cutting and cauterizing of tissue; and as a low voltage cautery tool where $I^2R$ losses create heat to cauterize the tissue.

Another principal object of the present invention is to provide an electro-cautery tool utilizing a capacitive type blade in which two conductors are separated by an insulator and driven by an alternating current.

Irrespective of the particular blade style, the present invention incorporates a piezo-ceramic or like transducer element for vibrating the blade sufficient to produce a cavitation effect, thereby preventing adherence of tissue debris on the blade. The transducer may be affixed to the blade member or disposed in the handle member in intimate contact with the blade so as to vibrate the blade producing cavitation at the interface between the tissue and the blade.

In one embodiment of the present invention, there is provided an electro-cautery surgical tool, including a base member of a conductive material, such as stainless steel or the like, the base material fashioned in the form of a surgical blade with a sharpened edge leading to a point, layers of insulation disposed on opposing sides of the blade, a second layer of conductive material deposited over the insulation material, and a plurality of geometrical gaps extending through the second conductive layer which may be formed by semiconductor technology techniques including sandblasting by masking, laser machining, chemical action, electrode discharge machining (EDM), electron beam drilling, ion milling, or grinding, to define a conductive comb-shaped electrodes on the opposing sides of the blade. Alternative embodiments of the present invention include opposing gaps on opposing surfaces of the blade, staggered gaps on opposing surfaces of the blade, holes partially through the second conductive portion to the first conductive portion of the blade, and a sandwiched alternating configuration of gaps.

Another alternative embodiment of the present invention comprises an electro-cautery tool which includes a conductive blade, a thick insulation layer extending across the conductive blade except at a defined sharpened cutting edge of the blade, a narrow conductor, such as a foil or the like, positioned slightly offset from the edge of the thick insulation, and a final thinner layer insulation covering the narrow conductor whereby the narrow conductor and the underlying blade conductor provide a capacitive effect for bioelectrically breaking down flesh.

An electrical-to-mechanical transducer, such as a piezo-ceramic, such as barium titanate, can be attached to or mechanically coupled to the surgical blade for vibrating the blade so as to provide a cavitation effect.

One significant aspect and feature of the present invention is an electro-cautery surgical blade which can be utilized in a plurality of modes including a standard surgical blade, an electro-cautery blade mode, or a mode where heat is produced during cauterization.

Another significant aspect and feature of the present invention is an electro-cautery surgical blade which uses state-of-the-art technology in producing the blade at minimized cost, thereby making the blade disposable.

A further significant aspect and feature of the present invention is an electro-cautery surgical blade which utilizes a capacitive relationship between two conductors.

It is a principal object hereof to provide an electro cautery surgical blade.

Another object is to provide an electro cautery surgical blade which is ultrasonically vibrated.

A further object of the present invention is to provide a surgical blade which is disposable and produced by state-of-the-art semiconductor integrated circuit manufacturing processes.

Yet another object of the present invention is a surgical blade which utilizes a capacitive effect by the spacing of two conductors, the one conductor being insulated from a blade conductor, the blade conductor including a sharp edge.

A still further object of the present invention is to utilize an electrical-to-mechanical transducer to vibrate the blade at a predetermined amplitude and frequency at any time during a surgical procedure thereby preventing build-up of debris on the surgical blade.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
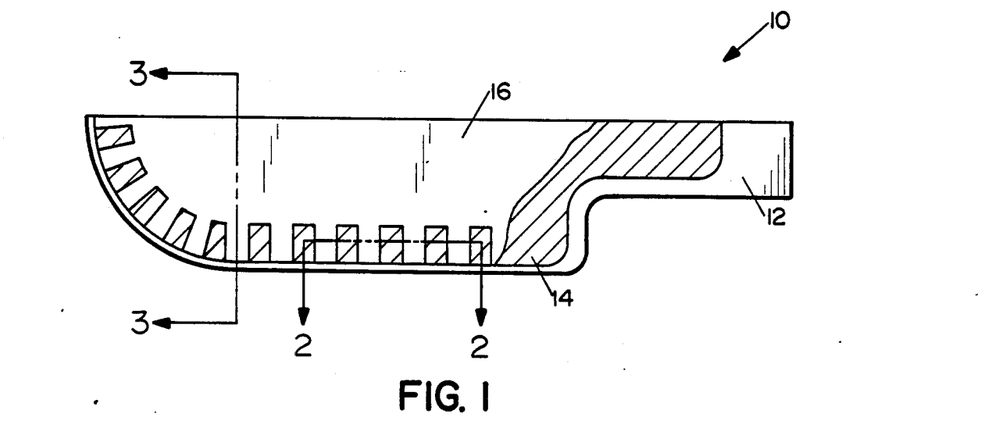
FIG. 1 illustrates a cross-sectional view of an electro cautery surgical blade.

FIG. 1 illustrates a cross-sectional view of the blade portion 10 of an electro-cautery surgical tool including a conductive base member 12, such as stainless steel or the like, which is capable of being ground or honed to a sharp cutting edge. Stainless steel is particularly suitable for surgical reasons in that it maintains a sharp edge, and it can be worked in a machining and manufacturing point of view, and is a material which is recognized in a surgical and medical sense by the Food and Drug Administration. An insulation layer 14 is deposited over the conductive base 12 on both of its sides by known processes in the art. A second conductive material 16 is deposited over the insulation material 14 in a predetermined pattern. A plurality of gaps may be formed along the edge, the gaps being of a finite height and width. Processes, such as sandblasting, laser machining, chemical etching, electrodischarge machining (EDM), electron beam drilling, ion milling, grinding or the like, may be used to form a comb-like conductive electrode with opposing gaps with insulating material between the teeth. Subsequently, a sharp cutting edge is honed on the base member 12. The blade can take any predetermined geometrical configuration including one having a sharp point, a rounded point as illustrated in FIG. 1, or any other geometrical figure depending upon the type of surgery as well as the surgeon's preference.

Figure 2:
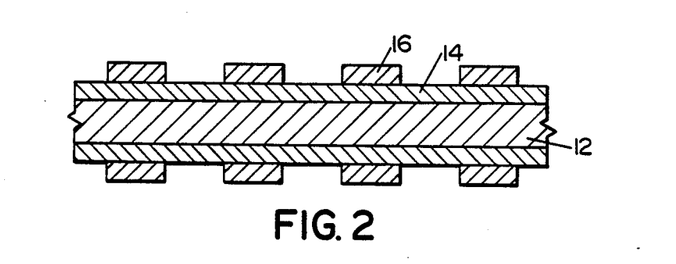
FIG. 2 illustrates a sectional view taken along line 2—2 of FIG. 1.

FIG. 2 illustrates a view taken along line 2—2 of FIG. 1 where all numerals correspond to those elements previousy described. The figure illustrates the opposing comb teeth and gaps which do not necessarily have to be opposed but can be staggered. Such opposing gaps are by way of example and for purposes of illustration only and not to be construed as limiting of the present invention.

Figure 3:
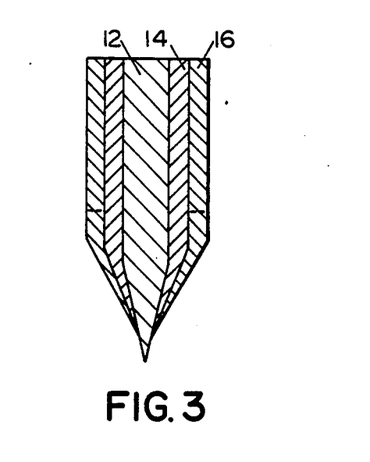
FIG. 3 illustrates a sectional view taken along line 3—3 of FIG. 1.

FIG. 3 illustrates an end view of FIG. 1.

Figure 4:
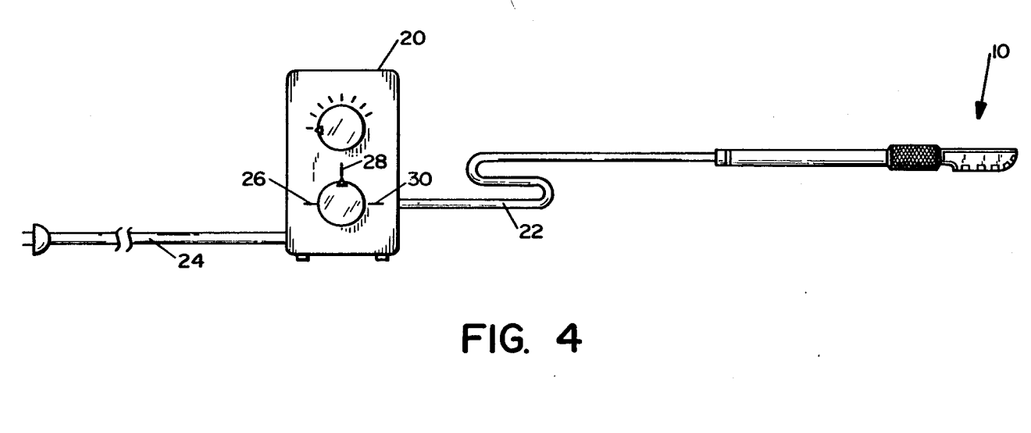
FIG. 4 illustrates the electro cautery surgical blade wired to a surgical power supply.

FIG. 4 illustrates the electro surgical blade 10 mounted in a holder and connected to a surgical power supply 20 by way of a surgical power cord 22 and a line cord 24. The surgical power supply is capable of operating in three modes, 26, 28, and 30. The first is a standard surgical blade mode 26 where no power is applied to the blade. The second mode is an electro-cautery mode 28 where high voltage is applied between the conductive members causing a slight discharge arc for cutting and cauterizing. The third mode involves a low voltage applied between the conductive elements where heat is produced by $I^2R$ losses for cauterization.

Figure 5:
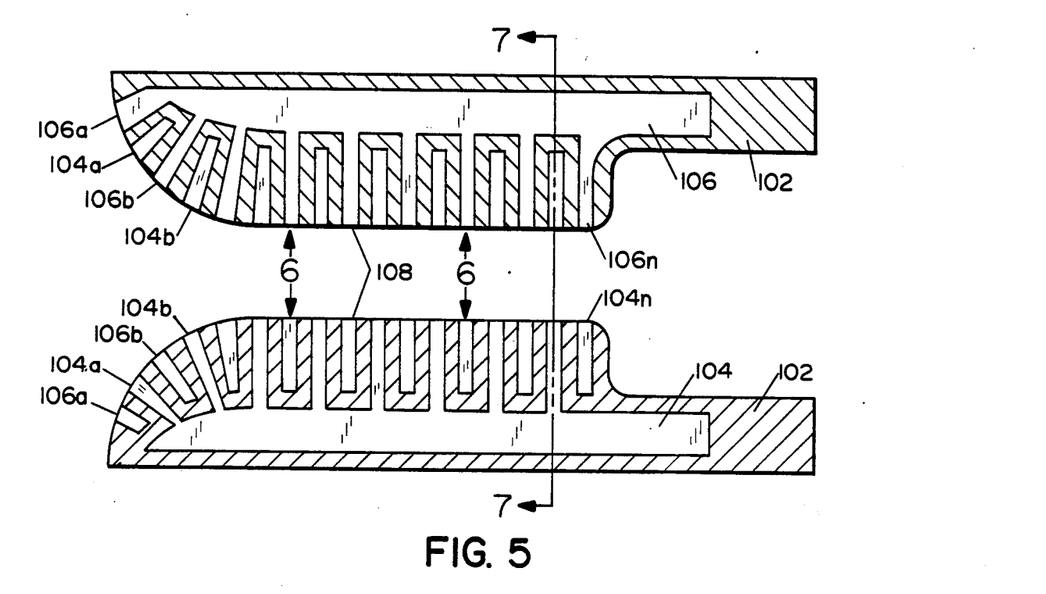
FIG. 5 is a folded view illustrating an alternative embodiment of an electro cautery surgical blade.

FIG. 5 illustrates a folded (two-sided) view of an electrode for electro cautery surgery including a non-conductive, insulative support 102, a first conductor 104 and a second conductor 106 arranged in an opposing matrix and electrically interconnected with respect to each other across the working edge 108. The conductors 104 and 106 are comb-shaped and the teeth extend to the respective opposite side of the support 102 with the extensions being interleaved with the teeth on that side. The particular tip of the cutting edge is ground to a sharp point 108.

Figure 6:
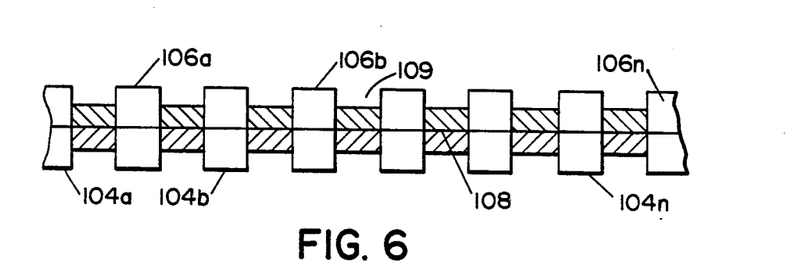
FIG. 6 illustrates a sectional view taken along line 6—6 of FIG. 5.

FIG. 6 illustrates a bottom view of FIG. 5 showing the particular configuration of the electrodes 104a–104n, 106a–106n, and insulative material 102.

Figure 7:
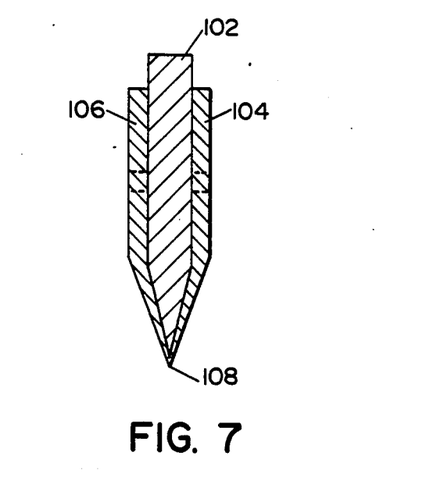
FIG. 7 illustrates a cross-sectional end view along line 7—7 of FIG. 5.

FIG. 7 illustrates a sectional view taken along line 7—7 of FIG. 5 where all numerals correspond to those elements previously described.

Figure 8:
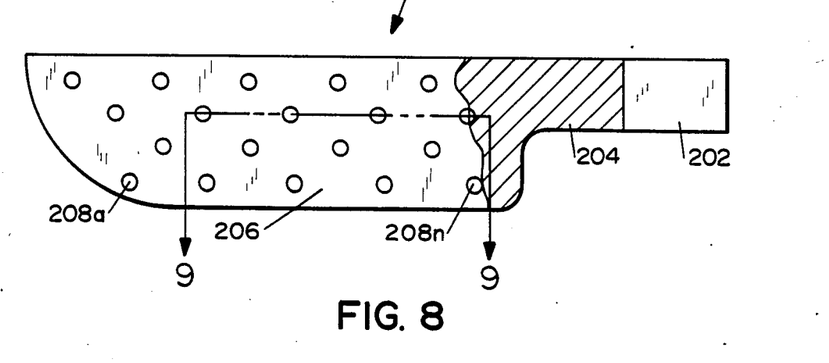
FIG. 8 illustrates a cross-sectional view of an alternative embodiment of a surgical blade.

FIG. 8 illustrates a cross-sectional view of an electro cautery surgical blade 200 including a conductive base member 202, an insulation layer 204, a second conductive material 206 deposited on the layer 104, a plurality of holes 208 extending through the material 206 and the insulation 204 to the base blade 202. The holes 208a–208n serve to distribute the electrical current in a predetermined fashion.

Figure 9:
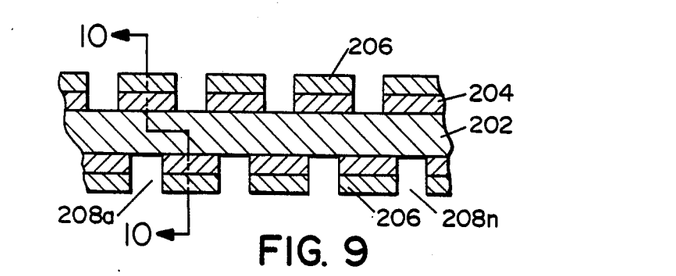
FIG. 9 illustrates a sectional view taken along line 9—9 of FIG. 8.

FIG. 9 illustrates a sectional view taken along line 9—9 of FIG. 8 where all numerals correspond to those elements previously described.

Figure 10:
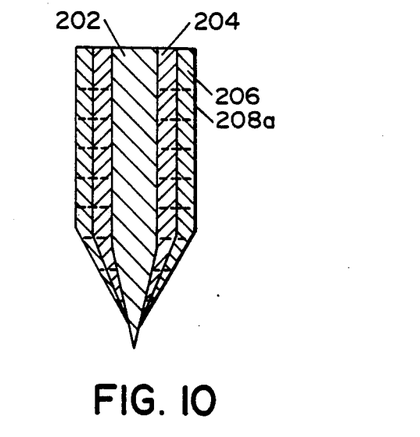
FIG. 10 illustrates a cross-sectional end view along line 10—10 of FIG. 9.

FIG. 10 illustrates a cross-sectional view taken along line 10—10 in FIG. 9 where all numerals correspond to those elements previously described.

Figure 11:
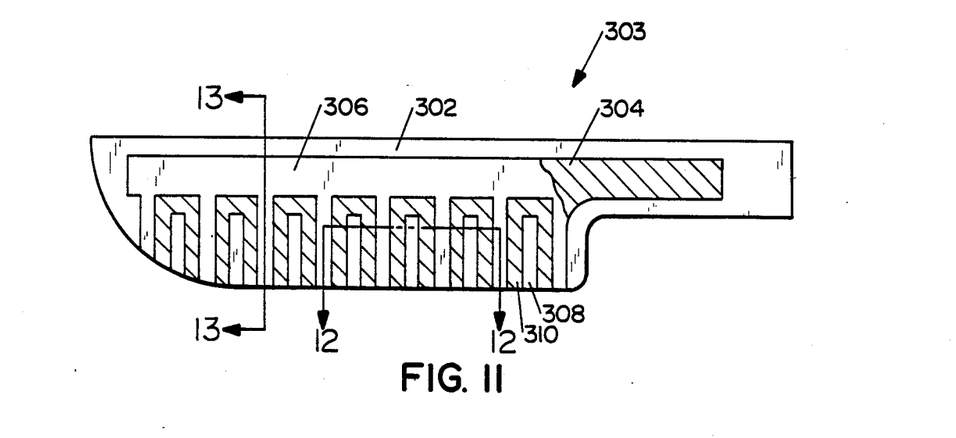
FIG. 11 illustrates another cross-sectional view of a further alternative embodiment.
Figure 12:
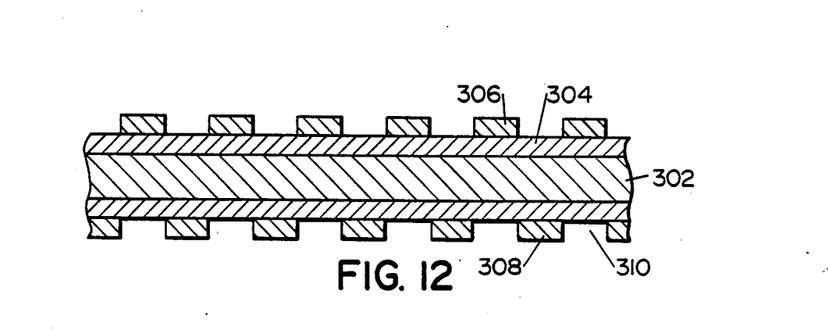
FIG. 12 illustrates a sectional view taken along line 12—12 of FIG. 11.

FIG. 11 illustrates a cross-sectional view of an electro-surgical blade 303 including a conductive base member 302, insulation layer 304, and a second conductive material 306 deposited in layer 304 and including a plurality of wrapped-around segments 308 and gaps 310 alternating therebetween, as also illustrated in the cross-sectional view of FIG. 12.

Figure 13:
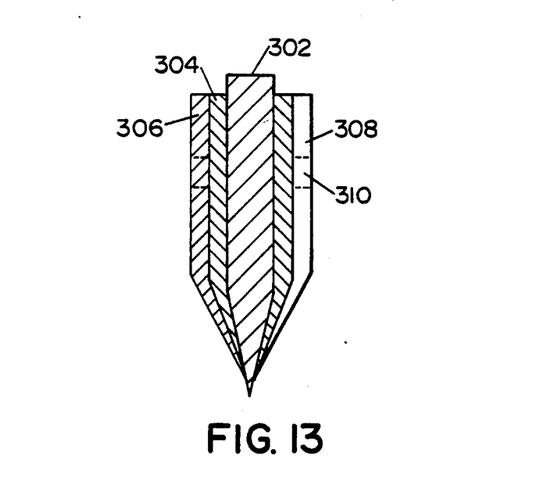
FIG. 13 illustrates a cross-sectional end view along line 13—13 of FIG. 11.

FIG. 13 illustrates a view taken along line 13—13 of FIG. 11 where all numerals correspond to those elements previously described.

MODE OF OPERATION

The electro-cautery surgical blades are connected to an electro-cautery power supply which supplies power for three modes of operation, those modes of operation being either a mode of operation as a standard surgical blade, a mode of operation as an electro-cautery blade where high voltage is applied between the conductive layers and the resulting discharge arc is used for cutting and cauterizing, or a mode of operation where the blade has applied to it a low voltage where heat is produced by the $I^2R$ losses for cauterization.

The insulative material can be a ceramic, glass, or other non-conductive material. The conductive material can be vapor-deposited or plated and photo-etched onto the insulative non-conductive material and can be silver, gold aluminum or the like. The base member should be a high-conductivity metal which has the property of being honed to a fine sharp edge. More so, a non-conductive insulative material which may be brought to an edge, such as glass or ceramic, with a photo-etched or vapor-deposited metal thereon is particularly desirable in this disclosed group of embodiments.

ALTERNATIVE EMBODIMENT—CAPACITIVE BLADE

Figure 14:
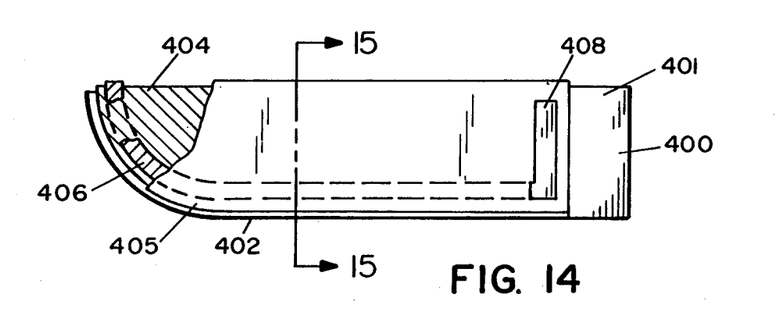
FIG. 14 illustrates a plan view of a capacitive surgical blade.
Figure 15:
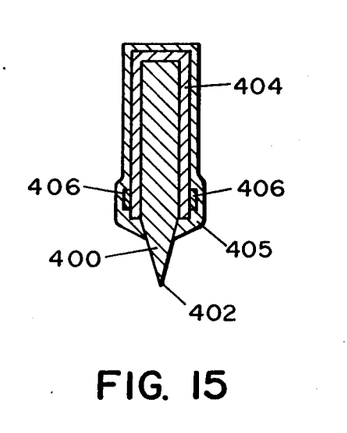
FIG. 15 illustrates a sectional view taken along line 15—15 of FIG. 14.

FIG. 14 illustrates a side view of a capacitive electro-cautery surgical blade including a blade conductor 400 with a sharp cutting edge 402 formed on the working edge thereof. The right end of the blade when viewed in FIG. 14 acts as a first electrical contact pad 401. A thick insulator 404, such as 0.005" to 0.015" thick, is positioned over the blade conductor 400, as best illustrated in the cross-sectional view of FIG. 15. A narrow conductor 406 of a finite thickness in the range of 0.01" to 0.03" and a predetermined width is positioned slightly offset above lowermost edge of the thick insulator 404, and as illustrated is in a plane parallel to the blade conductor 400. The narrow conductor 406 terminates at a second contact pad 408 isolated from pad 401, and wraps around the forward upper edge of the blade as illustrated in FIG. 14. A thin insulator 405 of a finite thickness of 0.001" to 0.002" is positioned over the top of the narrow conductor 406 and subsequently over insulator 404, and is offset slightly below the lower edge of the thick insulator 404. The contact pads 401 and 408 provide for connection to a source of electrical current for impressing a capacitive charge across the thick blade conductor 400, insulator 404, and the thin, narrow conductor 406, thereby providing for dielectric breakdown when the blade is brought into contact with the flesh during operation. The blade can mount in a blade holder, such as that illustrated in FIG. 18. The blade holder can include a screw or like for compression clamping about the blade and providing for electrical contact to the contact pads.

Figure 16:
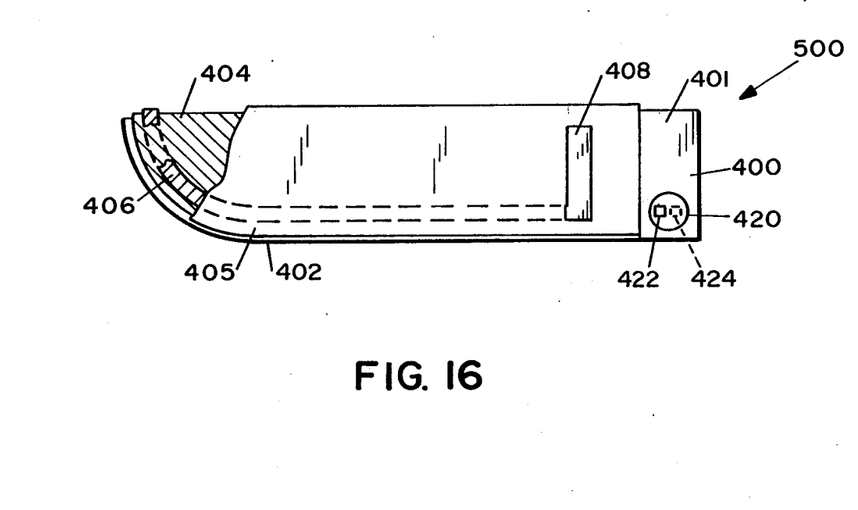
FIG. 16 illustrates a plan view of a capacitive surgical blade with an ultrasonic transducer.

FIG. 16 illustrates a plan view of a capacitive electro-cautery blade 400 where all numerals correspond to those elements previously described. An electrical-to-mechanical transducer, such as an ultrasonic transducer 420 is affixed to the blade and includes two contact pads 422 and 424 for supplying power from an alternating current source to the transducer 420. Contact pad 424 electrically and mechanically connects to the contact pad 401. The transducer 420 vibrates at a frequency determined by the power supply, and at an amplitude which provides a cavitation effect, at the selected frequency. The high frequency vibration of the blade prevents adherence of debris to the blade 400 during a surgical procedure. The transducer 420 can be powered independently or may be driven by the same power source used for energizing the blade.

ALTERNATIVE EMBODIMENT—RESISTIVE BLADE

Figure 17:
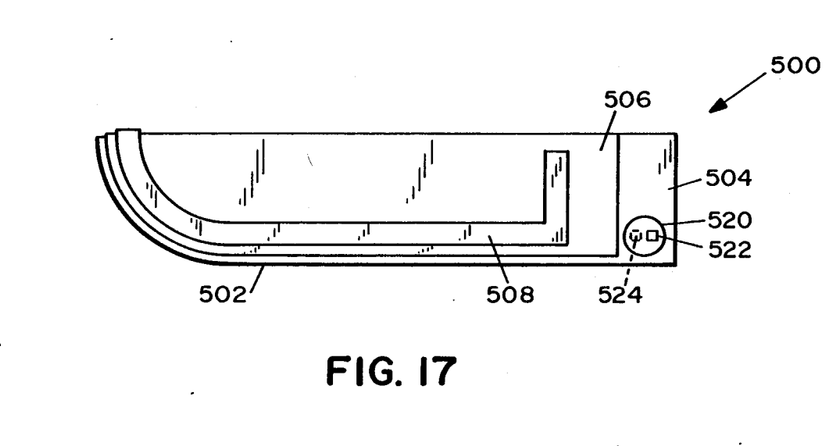
FIG. 17 illustrates a plan view of a resistive surgical blade with an ultrasonic transducer.

FIG. 17 illustrates a plan view of a resistive electro-cautery blade 500 including a sharpened edge 502, a first contact pad area 504, a layer of insulation 506 on the conductive base but exposing the cutting edge 502, and a wrap-around exposed metal surface 508 including a second contact pad 510 deposited on or affixed to the layer 506. The resistive blade is similar to that type of blade described previously in FIGS. 1–13. A transducer element 520, including contact points 522 and 524, is positioned in intimate contact with the contact surface 504. The contact point 524 mechanically and electrically connects to the contact pad 504. The operation of the blade of FIG. 17 in a vibratory mode is the same as the operation of FIGS. 14–16.

BLADE HOLDER

Figure 18:
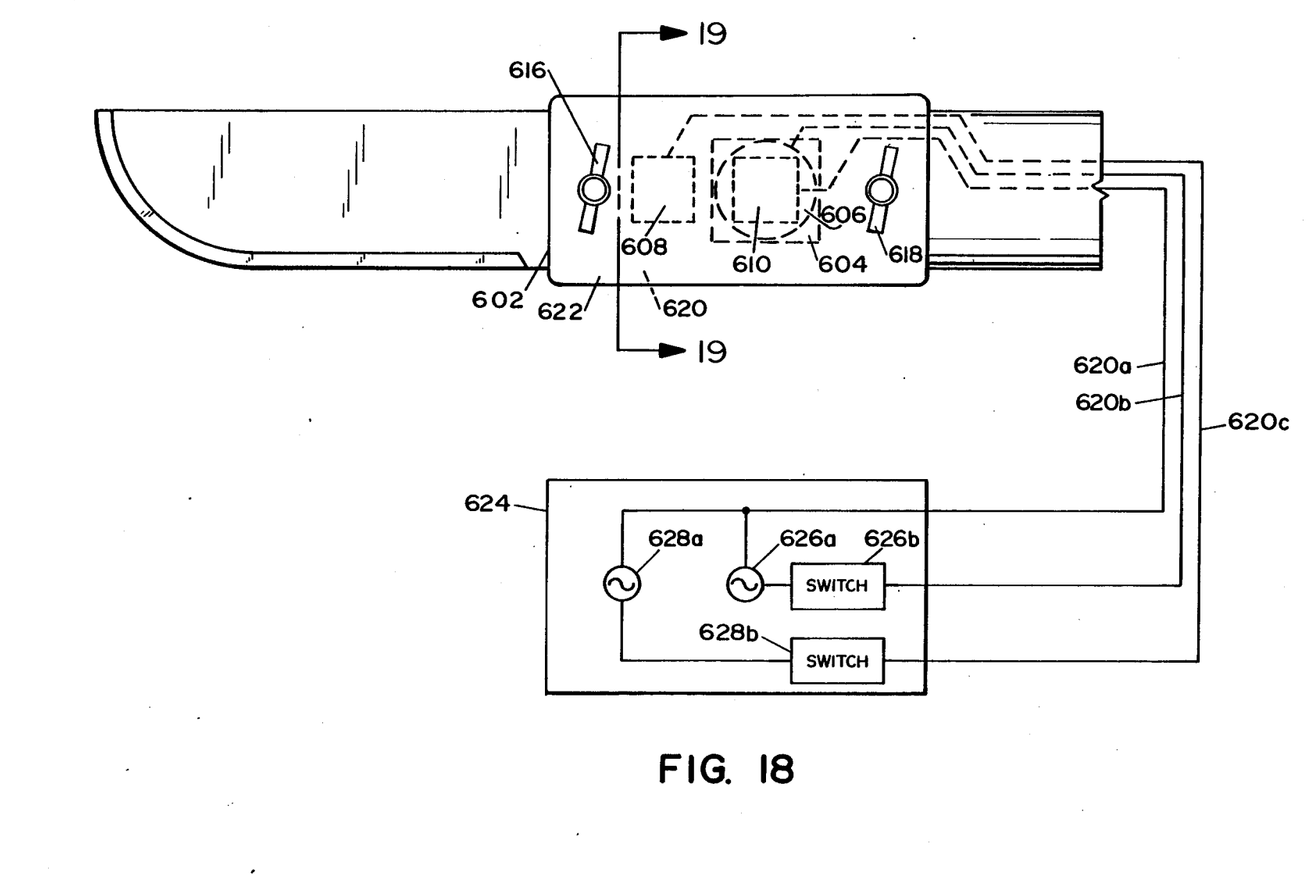
FIG. 18 illustrates a plan view of a blade holder with an ultrasonic transducer.
Figure 19:
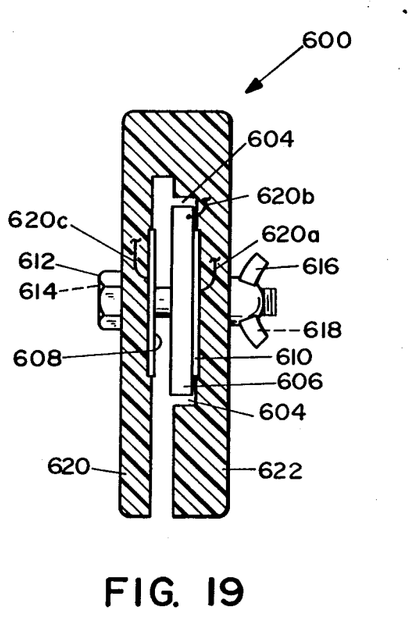
FIG. 19 illustrates a view taken along line 19—19 of FIG. 18.

FIG. 18 illustrates a plan view of a blade holder with a vibratory transducer, another alternative embodiment of the present invention. The blade holder 600 includes a slot 602 extending through a forward portion of the handle and upwardly from a lower edge of the handle into the handle as also illustrated in FIG. 19. There is also provided a cavity 604 for supporting piezo-electric transducer 606 which thus locates it next to a surgical blade all as later described in detail. The transducer 606, when mechanically compressed against the surgical blade, causes the surgical blade to vibrate in a direction transverse to the longitudinal axis of the blade during a power on condition. In the alternative, the cavity may be configured to accept the surgical blade with the transducer permanently affixed to the surgical blade. Then, of course, appropriate electrical contact pads would have to be provided to power the ultrasonic transducer.

The blade holder 600 also includes two contact pads 608 and 610 for making contact with a surgical blade so as to be able to selectively provide power to both the blade and the transducer 606. Screws 612 and 614 and wing nuts 616 and 618 provide for compression of the two halves of the blade holder 620 and 622 so as to compress the slit 602, and hold a surgical blade in frictional engagement within the holder 600.

A power source 624 including three power cables 620a–620c provides power to the surgical blade as well as the transducer. The power cables include a common wire 620a, a transducer wire 620b and a surgical blade power wire 620c. The power source 620 can be switchable and pulsed as required, including a transducer waveform source 626a and switching device 626b, and blade waveform source 628a and switching device 628b.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An electro-cautery surgical instrument comprising:
   (a) an electro-cautery surgical blade means including means for electrically cauterizing tissue; and
   (b) means for vibrating said surgical blade means at a frequency and amplitude to prevent the build-up of tissue debris thereon.

2. The surgical instrument of claim 1 wherein said electro-cautery blade means exhibits a capacitive effect.

3. The surgical instrument of claim 1 wherein said electro-cautery blade means causes heating of the tissue by a current flowing through said tissue as a resistive element.

4. The surgical instrument of claim 1 wherein said means for vibrating said surgical blade means is a piezo-ceramic transducer.

5. The surgical instrument of claim 4 wherein said transducer is affixed directly to said surgical blade means.

6. The surgical instrument of claim 1 wherein said means for vibrating said surgical blade means is a barium titanate piezo-ceramic transducer.

7. The surgical instrument of claim 1 and further including power source means electrically connected to said surgical blade means and to said means for vibrating said surgical blade means for powering said surgical blade means and said means for vibrating said surgical blade means.

8. In combination, a blade holder and a blade comprising:
   (a) a blade holder including a longitudinal slit for receiving a predetermined portion of said blade and including electrical power source contact pad connection means in said slit;
   (b) electrical-to-mechanical transducer means positioned in a distal portion of said blade holder;
   (c) mechanical compression means for drawing said slit into a substantially closed position about both said blade and said transducer means for urging said transducer means into engagement against said blade; and
   (d) said blade including a proximal portion, a working edge extending distally of said proximal portion, a first conductor extending across said blade, a first insulation layer disposed over said first conductor and up to said working edge of said blade, a second conductor extending generally parallel to said first conductor and spaced by said first insulation layer from said first conductor and from said working edge on at least one side of said blade, a second insulation layer covering said second conductor, and two or more electrical contact pads electrically connected to said first and second conductors and located on said proximal portion of said blade and operatively connected to said contact pad connection means in said slit for coupling electrical energy to said blade.

9. The combination of claim 8 wherein said transducer means is a piezo-ceramic.

10. The combination of claim 8 wherein said transducer means is a barium titanate piezo-ceramic transducer.

11. The combination of claim 8 wherein said transducer means is directly affixed on said blade.

12. The combination of claim 8 including power source means for powering said blade and power source means for powering said transducer means, each of said power source means being connected to said contact pad connection means of said surgical blade holder by a flexible cable.

13. The combination of claim 8 wherein said first conductor is a base member of said blade and said second conductor is parallel to and insulatively spaced from said base member to generate a capacitive field therebetween when an electrical potential is connected thereacross.

14. The combination of claim 8 wherein said first insulation layer is between 0.005 and 0.015 inches in thickness.

15. The combination of claim 8 wherein said second conductor is less than 0.030 inches in thickness.

16. The combination of claim 8 wherein said second insulation layer is between 0.005 and 0.0024 inches in thickness.

* * * * *